United States Patent
Shibuya et al.

(10) Patent No.: US 9,029,789 B2
(45) Date of Patent: May 12, 2015

(54) METHOD FOR DETECTING RADIATION, DEVICE THEREOF, AND POSITRON EMISSION TOMOGRAPHY SCANNER

(75) Inventors: Kengo Shibuya, Chiba (JP); Taiga Yamaya, Chiba (JP); Naoko Inadama, Chiba (JP); Fumihiko Nishikido, Chiba (JP); Eiji Yoshida, Chiba (JP); Hideo Murayama, Chiba (JP)

(73) Assignee: National Institute of Radiological Sciences, Chiba-shi (JP)

( * ) Notice: Subject to any disclaimer, the term of this patent is extended or adjusted under 35 U.S.C. 154(b) by 988 days.

(21) Appl. No.: 12/919,358

(22) PCT Filed: Apr. 9, 2008

(86) PCT No.: PCT/JP2008/057035
§ 371 (c)(1),
(2), (4) Date: Aug. 25, 2010

(87) PCT Pub. No.: WO2009/125480
PCT Pub. Date: Oct. 15, 2009

(65) Prior Publication Data
US 2011/0001049 A1  Jan. 6, 2011

(51) Int. Cl.
G01T 1/202 (2006.01)
G01T 1/29 (2006.01)
(52) U.S. Cl.
CPC .................... G01T 1/2985 (2013.01)
(58) Field of Classification Search
USPC ........................................................ 250/367
See application file for complete search history.

(56) References Cited

U.S. PATENT DOCUMENTS

| | | | |
|---|---|---|---|
| 7,193,208 B1 | 3/2007 | Burr et al. | |
| 2005/0236577 A1* | 10/2005 | Katagiri | 250/390.11 |
| 2006/0081899 A1 | 4/2006 | Fritzler et al. | |
| 2008/0128631 A1* | 6/2008 | Suhami | 250/370.09 |
| 2009/0159804 A1* | 6/2009 | Shibuya et al. | 250/363.03 |
| 2010/0127178 A1* | 5/2010 | Laurence et al. | 250/363.04 |
| 2010/0314546 A1* | 12/2010 | Ronda | 250/340 |

FOREIGN PATENT DOCUMENTS

| | | |
|---|---|---|
| JP | A-2002-296351 | 10/2002 |
| JP | A-2004-279057 | 10/2004 |
| JP | A-2005-114367 | 4/2005 |
| JP | A-2005-249411 | 9/2005 |
| JP | A-2006-113061 | 4/2006 |
| JP | A-2007-147598 | 6/2007 |
| JP | A-2008-51701 | 3/2008 |

OTHER PUBLICATIONS

Moses et al.; "PET Detector Modules Based on Novel Detector Technologies,"*Nuclear Instruments and Methods*; 1994; pp. 189-194; vol. A-353, University of California., Berkeley.

(Continued)

*Primary Examiner* — Michael G Lee
*Assistant Examiner* — David Tardif
(74) *Attorney, Agent, or Firm* — Oliff PLC

(57) ABSTRACT

A light receiver for detecting incident time is installed on the side of a radiation source of a scintillator (including a Cherenkov radiation emitter), and information (energy, incident time, an incident position, etc.) on radiation made incident into the scintillator is obtained by the output of the light receiver. It is, thereby, possible to identify an incident position and others of radiation into the scintillator at high accuracy.

14 Claims, 16 Drawing Sheets

(56) References Cited

OTHER PUBLICATIONS

Shibuya et al.; "Time-of-Flight PET;" *Radioisotopes*; Jul. 2006; pp. 33-44; vol. 55, No. 7; Japan Radioisotope Association.

International Search Report dated Jul. 15, 2008 in corresponding international Application No. PCT/JP2008/057035 (with translation).

\* cited by examiner (A) Conventional PET scanner (B) TOF-PET scanner (A)

(B)

(A)

(B)

(C)

METHOD FOR DETECTING RADIATION, DEVICE THEREOF, AND POSITRON EMISSION TOMOGRAPHY SCANNER

TECHNICAL FIELD

The present invention relates to a method for detecting radiation, the device thereof, and a positron emission tomography scanner. The present invention relates in particular to a method for detecting radiation which is capable of obtaining information (energy, incident time, an incident position, etc.) on radiation made incident into a scintillator (including a Cherenkov radiation emitter) at high accuracy, the device thereof and a positron emission tomography scanner which utilizes the device.

BACKGROUND ART

The positron emission tomography scanner (PET) is a nuclear-medicine imaging equipment utilizing a positron emission nuclide, for use in various applications such as diagnosis of cancers and molecular imaging.

The positron emission nuclide is an isotope such as $^{18}$F which is unstable due to an excessively large number of protons in an atomic nucleus as compared with a number of neutrons, having the radioactivity of emitting positrons and neutrinos in association with β+ decay. The thus emitted positron, the antimatter of electron, undergoes pair annihilation when colliding with an electron and the mass of the positrons and electrons is all converted to energy. This energy is radiated in a form of high-energy electromagnetic waves which is called annihilation radiation. Because of the law of conservation of momentum before and after pair annihilation, mainly two annihilation radiation photons are emitted at the same time and approximately in the opposite direction. Strictly speaking, although there is a case where a single photon or three or more photons are emitted, the percentage is less than 1% of the total and, therefore, to be negligible in the PET imaging. Where two photons are emitted, each of the energies corresponds to the mass of one (positron) electron, that is, approximately, 511 keV.

The principle of imaging is the coincidence of annihilation radiation. Where radiation of 511 keV is determined substantially at the same time by two mutually opposing radiation detectors, it is most likely that positrons have undergone pair annihilation on a straight line connecting these two radiation detectors. This information is collected, as shown in FIG. 1(A), by using many radiation detectors 16 arranged around a scanned substance 10 and reconstructed by a mathematical approach similar to that used in an X-ray CT. Thereby, it is possible to obtain a tomographic image similar to the distribution of a positron emission nuclide 12 in the test substance 10. In this drawing, the numeral 18 depicts a bed.

Therefore, a performance required for the radiation detector 16 is to determine an incident position, energy and incident time of the annihilation radiation 14 as accurately as possible. Here, substantially at the same time means, in general, time within 15 nanoseconds (nano is a prefix which denotes a factor of $10^{-9}$), where a radiation detector is able to determine time more accurately, the time is to be less than 10 nanoseconds or less than 5 nanoseconds. If a time frame (coincidence time window) for judging incidence of two annihilation radiation photons to be one annihilation radiation set generated from one pair annihilation, and regard as being at the same time is shortened, it is less likely that a plurality of annihilation radiation photons resulting from different pair annihilation are mistakenly combined. Therefore, determination accuracy can be enhanced to improve a signal-to-noise ratio. In addition, the above-described combination of annihilation radiation photons detected by determining a time window is referred to as coincidence counting or coincidence.

It is known that where a capacity of processing an electric signal from the radiation detector 16 to determine the incident time of the annihilation radiation 14 is, in general, less than 1.5 nanoseconds, time-of-flight (TOF) of annihilation radiation is utilized, with the time window kept in a range which will not cause counting leakage in a correct combination of annihilation radiation photons, thereby improving a signal-to-noise ratio in a positron emission tomography (PET) scanner. For example, where pair annihilation takes place at the centers of two opposing radiation detectors, two annihilation radiation photons arrive at the radiation detectors at the same time. Further, where pair annihilation takes place at a coordinate (spatial coordinate) closer to one of the radiation detectors, annihilation radiation will arrive earlier at the closer radiation detector. In other words, a difference between the arrival time at one radiation detector and that at the other radiation detector is determined, it is possible to convert the time difference to a spatial difference between a distance from a spatial coordinate where pair annihilation takes place to one radiation detector and a distance from there to the other radiation detector. In a PET scanner which does not utilize conventional time-of-flight as shown in FIG. 1(A), information obtained from one set of coincidence is a straight line including a spatial coordinate where pair annihilation is considered to have taken place. However the use of time-of-flight makes it possible to narrow down to a certain region on the straight line like a time-of-flight type PET (TOF-PET) scanner shown in FIG. 1(B). The narrowing-down accuracy is determined depending on the time resolution of the scanner concerned. As the determination accuracy is increased, information on a position of pair annihilation is increased to result in enhancement of a signal-to-noise ratio (refer to IEEE Trans. Nucl. Sci., Vol. 50, No. 5, pp. 1325-1330, 2003, by W. W. Moses). Therefore, it is preferable that radiation detectors to be loaded on the TOF-PET have higher time determination accuracy.

In addition, where the capacity for determining the incident time of annihilation radiation is, in general, less than 100 picoseconds all over the scanner (pica is a prefix denoting a factor of $10^{-12}$), not only a signal-to-noise ratio but also the spatial resolution of a tomographic image is expected to be enhanced. Technology for enhancing the time resolution of radiation detectors has been strongly requested.

The concept of the TOF-PET scanner utilizing difference of the time-of-flight of annihilation radiation has been known since the 1980s (refer to IEEE Trans. Nucl. Sci., Vol. 28, No. 6, pp. 4582-4589, 1981 by T. Tomotani). However, at the technical level at that time, a scintillator and a radiation detector used as a radiation detecting element as well as a circuit for processing electric signals from the radiation detector were insufficient in performance and others, and therefore no improvement was made in a signal-to-noise ratio. At the present time, scintillators excellent in response speed such as LSO (lutetium silicate to which a small quantity of cerium is added) and LYSO (a mixed crystal of LSO with yttrium silicate to which a small quantity of cerium is added) have been developed. Further, a photomultiplier tube (PMT) used as a light receiver for detecting scintillation light caused by interaction with radiation is also improved in time determination accuracy. Since integrated circuit technologies for specific uses are also enhanced, it has been confirmed that a TOF-PET scanner utilizing difference of the time-of-flight of annihilation radiation is superior to a conventional PET scanner in performance of a signal-to-noise ratio. Therefore, there is strong demand for a radiation detector more excellent in time resolution. When the signal-to-noise ratio is enhanced, it is possible to shorten the time necessary for positron emission tomography and decrease the dosage of a radiopharmaceutical to be administered to a subject.

As shown in FIG. 2, a first error parameter of detection time is caused by a difference in transfer speed between annihilation radiation 14 and scintillation light 24 within a scintillator 22. In the drawing, the numeral 20 depicts a light receiver such as a photomultiplier tube.

The flight speed of the annihilation radiation 14 is equal to light speed c under a vacuum (approximately 300,000 km per second) either under a vacuum or in a medium. On the other hand, the scintillation light 24 is approximately equal to c in flight speed in the atmosphere but reduced in speed to c/n in a scintillator. Here, n denotes a refractive index of the scintillator and, in general, a value greater than 1.0.

Since annihilation radiation at 511 keV is greater in penetration force, a scintillator 22 having the thickness of a few centimeters is, in general, used for effective detection.

As shown on the right side in FIG. 2(A), where the annihilation radiation 14 interacts with the scintillator 22 in the vicinity of an upper end of the scintillator 22, the scintillation light 24 needs to fly at a long distance inside the scintillator 22 until arriving at the light receiver 20. On the other hand, as shown on the left side in FIG. 2(A), where it interacts therewith in the vicinity of a lower end of the scintillator 22, the scintillation light 24 will fly at a short distance until arriving at the light receiver 20. In other words, as shown in FIG. 2(B), apparent detection time is made earlier in a case where the annihilation radiation 14 flies at a long distance inside the scintillator 22, with the flight speed c kept, and the light is converted to the scintillation light 24 with the flight speed c/n immediately before the light receiver 20.

Here, where in determining one annihilation radiation set respectively by two radiation detectors, scintillation light is generated in the vicinity of an upper end of a scintillator at one detector and scintillation light is generated in the vicinity of a lower end of the scintillator at the other detector, a spatial coordinate of pair annihilation expected by a difference in the detection time is made closer to the other radiation detector than in actuality. Therefore, if a difference in the detection time resulting from a difference in transfer speed between annihilation radiation and scintillation light in the scintillator is corrected, it is possible to increase the information accuracy of difference of the time of flight. In addition, in FIG. 2(A), in order to simplify the principle, one scintillation photon is representatively emitted directly below per annihilation radiation. In actuality, several thousands or tens of thousands of photons are emitted, and a direction in which they are emitted is not necessarily limited to being directly below. Further, since some of the photons are absorbed by a boundary surface of the scintillator, a reflective material and others, all the photons do not necessarily arrive at a light receiver.

As illustrated in FIG. 3(A) a second error parameter of detection time is caused by a difference in the distance of a channel where the scintillation light 24 is transmitted through the scintillator 22. The scintillation light 24 is partially made incident directly into the light receiver 20, however, in general, more than half of the photons are reflected more than once on an upper surface or side surfaces of the scintillator 22 and then made incident into the light receiver 20. For example, as shown on the right side in FIG. 3(A), the scintillation light 24 that generated in the vicinity of an upper end of the scintillator 22 and radiated above arrives immediately at the upper end of the scintillator 22 and goes downward by being reflected by a reflective material and others covering the upper surface of the scintillator 22. On the other hand, as shown on the left side in FIG. 3(A), the scintillation light 24 radiated upward from the vicinity of a lower end of the scintillator 22 flies by a length of the scintillator 22 until being reflected downward at the upper end of the scintillator 22. Further, where the scintillation light 24 is emitted, with an angle kept in a lateral direction, a transmission channel will change by reflection on side surfaces of a scintillator. Further, where scintillators are arrayed in all directions two- or three-dimensionally, reflection or refraction among the scintillators also allows the transmission channel to change. As the transmission channel is made longer, the scintillation light 24 takes a longer time accordingly for arriving at the light receiver 20, and the time for determining the detection of annihilation radiation is delayed.

FIG. 3(B) shows a result in which LSO crystals, each of which measures 1.45 mm×1.45 mm×4.50 mm, are arrayed in a square shape by 32 pieces×32 pieces, which is prepared as one stage (layer), and in order to detect a position at which annihilation radiation interacts with scintillator crystals at higher accuracy, the thus prepared stage is stacked in four stages to give a crystal block, and based on this crystal block, calculation has been made for a transmission channel of scintillation light and the transmission time thereof. Here, a first layer in the drawing is closest to a radiation source and a fourth layer is furthest from there. In order to show the principle simply, a relationship between the number of photons arriving at a light receiver and elapsed time where one hundred thousands of photons are emitted at a reference time in random directions from the center of each crystal which has been selected at the center of each stage is shown. It is apparent therefrom that not only is the arrival time of a first photon different depending on a distance of a straight line between a light-emitting coordinate inside a scintillator crystal which has emitted light and a light receiver, but also there are times when the number of arriving photons is greatest and a second peak resulting from reflection on an upper surface of the crystal. If the thus generated difference in detection time due to a difference in the distance of a transmission channel of scintillation light is corrected, it is possible to increase the information accuracy of difference of the time of flight.

A third error parameter of the detection time is a difference in the output wave of a light receiver caused by a difference in the transmission channel. As apparent from FIG. 3(B) showing the time distribution of light (input) arriving at the light receiver, time necessary from arrival of the first photon from each layer to the time when the number of arriving photons is greatest is different depending on each layer. It is also apparent from the shape of the graph that the trend of increasing the number of photons with the lapse of time is different. In order to determine the time from an output wave of the light receiver in the simplest way, first, a threshold value is set to avoid confusion of noises with a signal, an output in excess of the threshold value is regarded as a signal, and time in excess of the threshold value is given as detection time. If the definition is made common in all the light receivers, there will be no difference resulting from a definition method. However, in this method, as shown in FIG. 3(C), where an output signal is relatively large (for example, a fourth layer), the threshold value is exceeded soon after arrival of a first photon, but where the output signal is relatively small (for example, a first layer), the threshold value is exceeded only around the time when the output is maximum. Therefore, the time to be determined is deviated depending on a magnitude of the signal. Therefore, in actuality, a more sophisticated determination method such as a constant fraction method in which time is not deviated depending on a magnitude of the output signal is extensively used (refer to Radiation Handbook, third edition, pp. 753, 2001, published by Nikkan Kogyo Shimbun).

However, since even the constant fraction method capable of coping with the change in magnitude of an output signal is unable to cope with the change in waveform of the output signal, a deviation of time which is determined by a difference in whether a signal rises abruptly or slowly is caused. Thus, if correction is made for a difference in the detection time which is caused by a difference in the output waveform of a light receiver resulting from a different transmission channel of scintillation light, it is possible to increase the information accuracy of difference of the time of flight. This is effective not only in the constant fraction method but also in a leading edge method or other determination-making methods. A difference can be corrected, for example, on the basis of a gradient found when a signal rises or the change thereof.

Technology for correcting detection time by utilizing only information on a light emitting position in the depth direction by the use of a radiation detector as shown in FIG. 4, in place of information on a three-dimensional position (light emitting position) is already known (refer to IEEE Trans. Nucl. Sci., Vol. 53, No. 1, pp. 35-39, 2006, by T. Tsuda et al.). In the drawing, the numeral 40 depicts a radiation detector (referred to as a DOI detector) which is capable of obtaining information on depth of interaction (DOI) and made up of, for example, a 256-channel position-sensitive-type photomultiplier tube (PS-PMT) 21 and a scintillator crystal block 23 stacked, for example, in four layers by 6×6 proposed by the applicant in Japanese Published Unexamined Patent Application No. 2004-279057.

According to the above-described DOI detector, it is possible to obtain information on depth of interaction.

However, the DOI detector stacked in four layers as shown in FIG. 4 has following problems. Namely, a first layer on the side of a radiation source is greatest in TOF difference (delay) and lowest in time resolution due to a long distance to the PS-PMT 21 withal the fact that the number (frequency) of light emitting events by incident radiation is greatest. On the other hand, a fourth layer on the side of a light receiver is smallest in TOF difference (delay) and highest in time resolution due to the nearest distance to the PS-PMT 21, but the fourth layer is not effectively utilized because the number of events is smallest.

FIG. 5 shows the respective responses of four layers in a conventional DOI detector which is not subjected to TOF correction and time resolution of the detector as a whole. In this example, the time resolution (half bandwidth FWHM) of the radiation detector as a whole was 361.4 ps.

On the other hand, where TOF correction was made in every layer, as shown in FIG. 6, the time resolution of the radiation detector as a whole was improved to be 324.1 ps. However, this was still insufficient.

DISCLOSURE OF THE INVENTION

The present invention has been made to solve the above-described conventional problems, an object of which is to obtain information (energy, incident time, an incident position, etc.) on radiation made incident into a scintillator (including a Cherenkov radiation emitter) at high accuracy.

As shown in FIG. 7, the inventor made the following arrangement, that is, a radiation detector 40 was placed upside down, the PS-PMT 21 was installed on the side of a radiation source, a layer which is nearest to the PS-PMT 21 and small in TOF difference and highest in time resolution was given as a first layer to be made the greatest in the number of events, but a fourth layer which was greatest in distance from the PS-PMT 21, greatest in TOF difference and lowest in time resolution was made to be the smallest in the number of events.

FIG. 8 shows a result of an experiment where under the same determination conditions as those of FIG. 4, as shown in FIG. 7, the radiation detector 40 was placed upside down, and a first layer highest in time resolution was made greatest in detection rate. However, as with FIG. 6, TOF correction was also performed in every layer. In this instance, it was confirmed that, as compared with a case where only TOF correction was made, the radiation detector was placed upside down to improve the time determination accuracy, by which the time resolution of the radiation detector as a whole was enhanced to be 297.7 ps. As described so far, it is effective that a positional relationship between the light receiver and the scintillator is reversed and TOF correction is also made.

Here, the light receiver and a circuit portion thereof installed on the side of the radiation source are scatterers for annihilation radiation. However, experiments conducted by the inventor have found no hindrance in identifying an incident position of radiation strong in penetration force. FIGS. 9 (A), (B) and (C) show the arrangements in an experimentation conducted for confirmation, while FIG. 10, FIG. 11 and FIG. 12 show the respective results. FIG. 9(A) shows an example where, as with a conventional example, a flat panel-type position sensitive photomultiplier tube 31 (H9500 model by Hamamatsu Photonics K.K.) is installed on the opposite side of a radiation source 8 of a scintillator 34, FIG. 9(B) shows an example where in the same arrangement as that of FIG. 9(A), a PS-PMT 31' is installed as a scatterer also above the scintillator 34, and FIG. 9(C) shows an example where according to the present invention, the PS-PMT 31 is installed on the side of the radiation source 8 of the scintillator 34. In these drawings, numerals 32 and 32' depict a circuit substrate portion.

As apparent from FIG. 12, the arrangement of the present invention shown in FIG. 9(C) has improved an energy resolution $\Delta E/E$ to be 9.2% (the dotted line in FIG. 12), as compared with the arrangement of FIG. 9(A) (the solid line in FIG. 10, $\Delta E/E=10.0\%$) and the arrangement of FIG. 9(B) (the dotted line in FIG. 11, $\Delta E/E=10.1\%$). The energy resolution indicates that as its value is smaller, the energy of radiation made incident into a radiation detector is determined at higher accuracy. The fact that the arrangement of FIG. 9(A) (10.0%) is similar in value to the arrangement of FIG. 9(B) (10.1%) has demonstrated that the inserted PS-PMT 31' gives only a slight influence to energy resolution as a scatterer. Further, the fact that the arrangement of FIG. 9(C) (9.2%) is smaller in value than the arrangement of FIG. 9(A) (10.0%) has demonstrated the superiority in capacity for obtaining information on energy of incident radiation from a light signal emitted from a scintillator. Therefore, an object to which the present invention is applicable is not limited to a TOF-PET which gives priority to time resolution but effectively used in a conventional PET in which a higher energy resolution is preferable. Further, a part closer to a radiation source of the scintillator (an upper part in the drawing) interacts with radiation at a higher frequency than a part distant from the radiation source (a lower part in the drawing). Thus, it is apparent from the result of this experiment that even if scintillators are not stacked, a light receiver is installed on the side of the radiation source of a scintillator, thereby enhancing the performance of the radiation detector.

The present invention has been made on the basis of the above findings, that is, a light receiver for detecting incident time is installed on the side of a radiation source of a scintillator (including a Cherenkov radiation emitter), thereby obtaining information on radiation (energy, incident time (timing information), an incident position, etc.) through the output of the light receiver, thus solving the above problems.

As being superficially similar to the present invention, an idea that, as shown in FIG. 13, an avalanche photodiode (APD) 36 for obtaining information on a position and energy is installed on the side of the radiation source of a scintillator 32 and a PMT 21 for obtaining information on time and others is installed on the opposite side has been proposed (refer to IEEE Trans. Nucl. Sci., Vol. 41, No. 4, pp. 1441-1445, 1994, by W. W. Moses et al.). However, the APD is slow in response and not a main detector for determining the incident time.

The present invention also provides a radiation detecting device which is constituted with a light receiver for detecting incident time which is installed on the side of a radiation source of a scintillator (including a Cherenkov radiation emitter) and a means for obtaining information on radiation made incident into a scintillator by the output of the light receiver (for example, a processing circuit at a back stage).

Here, the light receiver may be installed only on the side of the radiation source of the scintillator.

Alternatively, the light receiver may be installed on the side of the radiation source of the scintillator and a light receiver assisting thereto is installed on the opposite side of the scintillator or on a side surface.

Further, a radiation detector made up of the scintillator and the light receiver may be given as a DOI detector.

Further, a combination of the scintillators with the detectors may be stacked.

Still further, a radiation detector to be made a pair may be installed so as to be opposite behind the radiation source, thus making it possible to determine coincidence and time of flight.

In addition, radiation detectors may be arrayed in a ring shape so as to surround the radiation source and a corn-shaped light guide is installed between each scintillator and each light receiver, thus making it possible to narrow down a diameter of the light-emitting light path with respect to a diameter of the incident light path to the light guide.

The present invention also provides a positron emission tomography scanner having the above-described radiation detecting device.

BEST MODE FOR CARRYING OUT THE INVENTION

Figure 1:
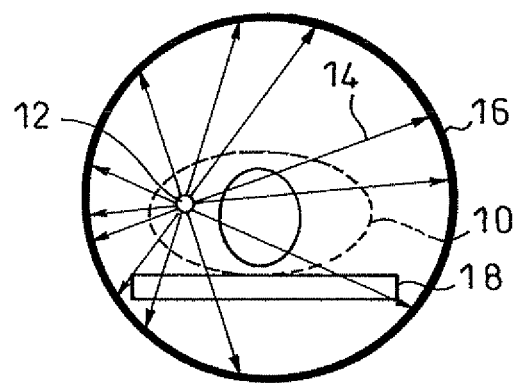
FIG. 1(A) is a cross sectional view showing a brief constitution of a conventional PET scanner and FIG. 1(B) is a cross sectional view showing a conventional TOF-PET scanner.
Figure 1:
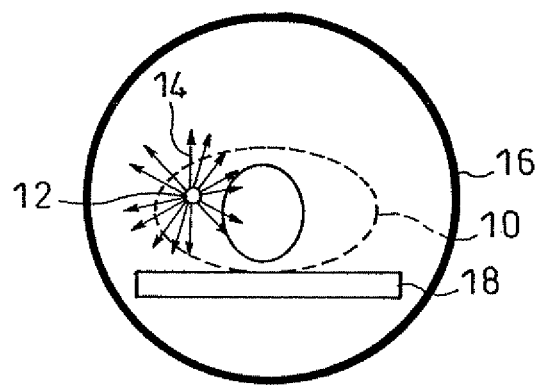
Figure 2:
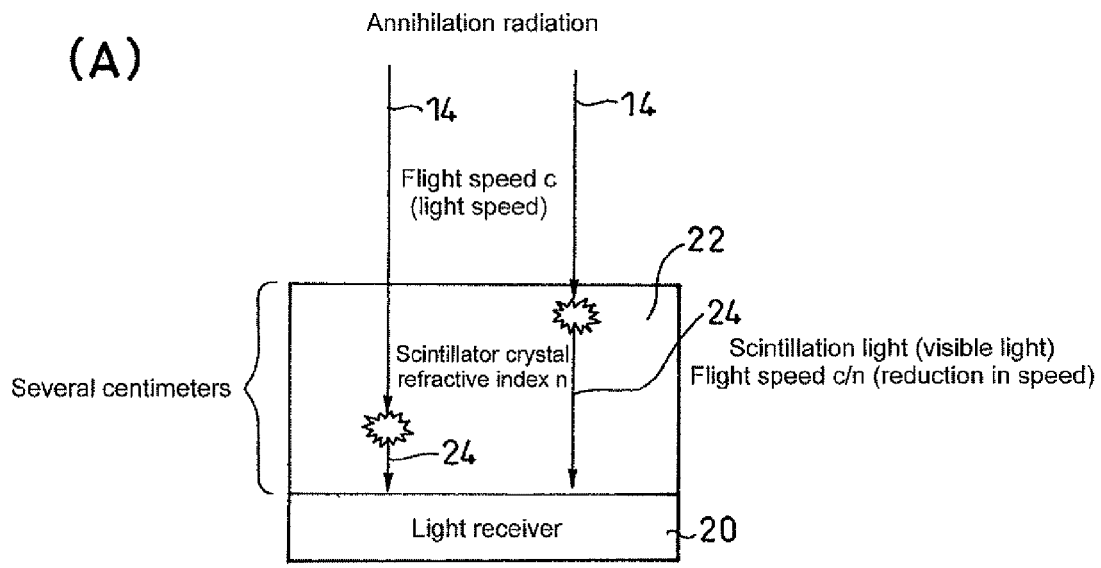
FIG. 2(A) is a cross sectional view for explaining one of the conventional problems and FIG. 2(B) is a time chart for explaining one of the conventional problems.
Figure 2:
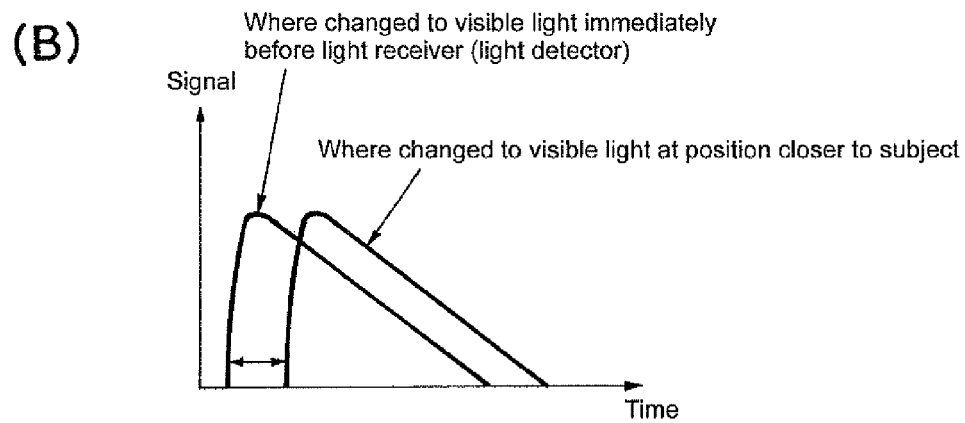
Figure 3:
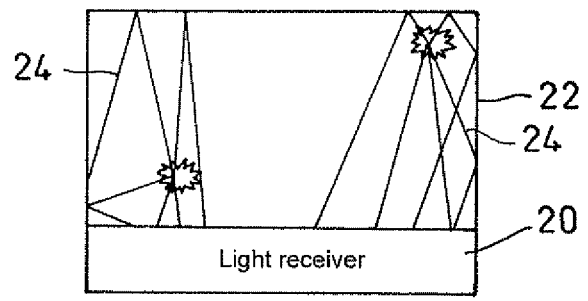
FIG. 3(A) is a cross sectional view for explaining other conventional problems and FIG. 3(B) and FIG. 3(C) are time charts for explaining other conventional problems.
Figure 3:
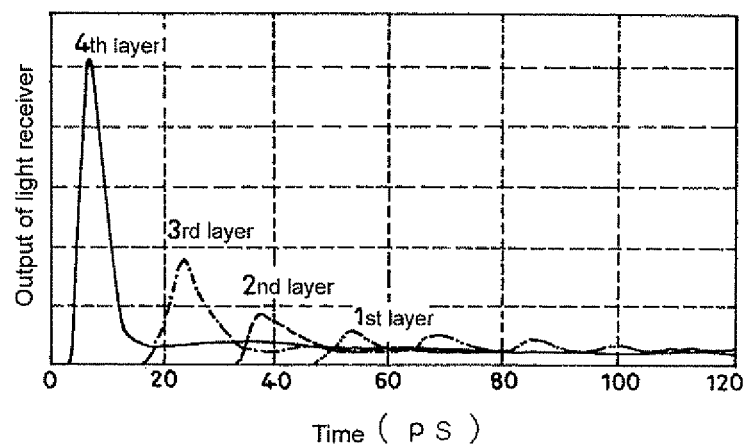
Figure 3:
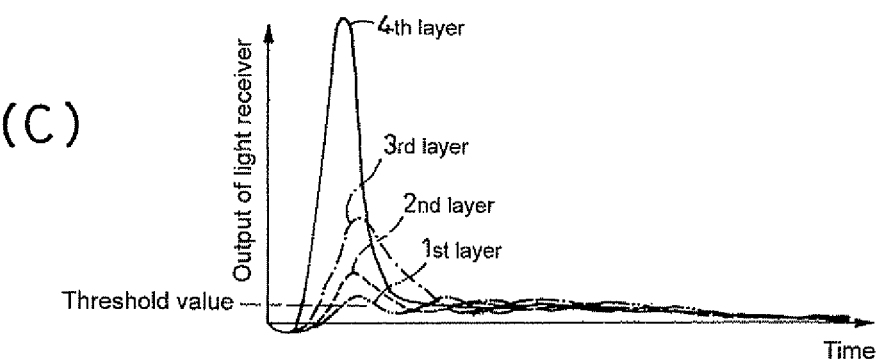
Figure 4:
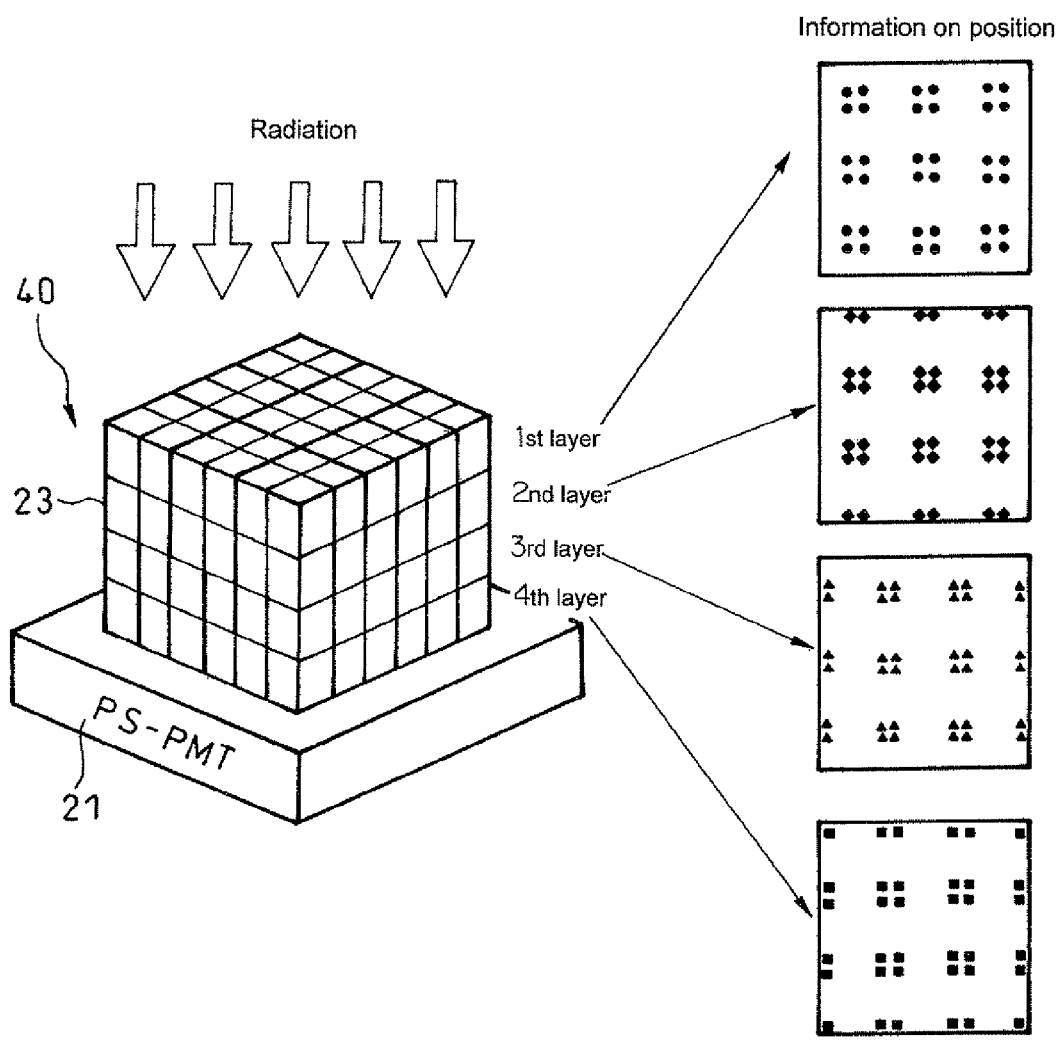
FIG. 4 is a perspective view for explaining one conventional solution method.
Figure 5:
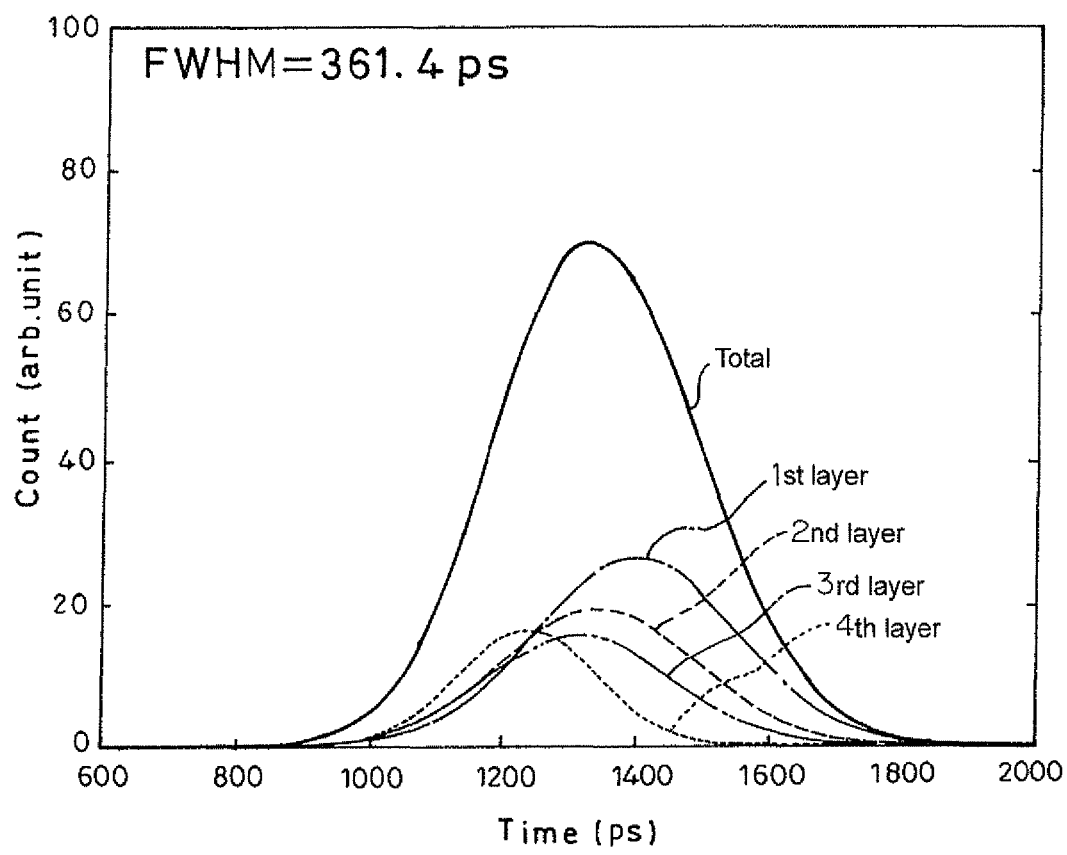
FIG. 5 is a drawing showing responses of individual layers in a conventional DOI detector free of TOF correction and the time resolution of the detector as a whole.
Figure 6:
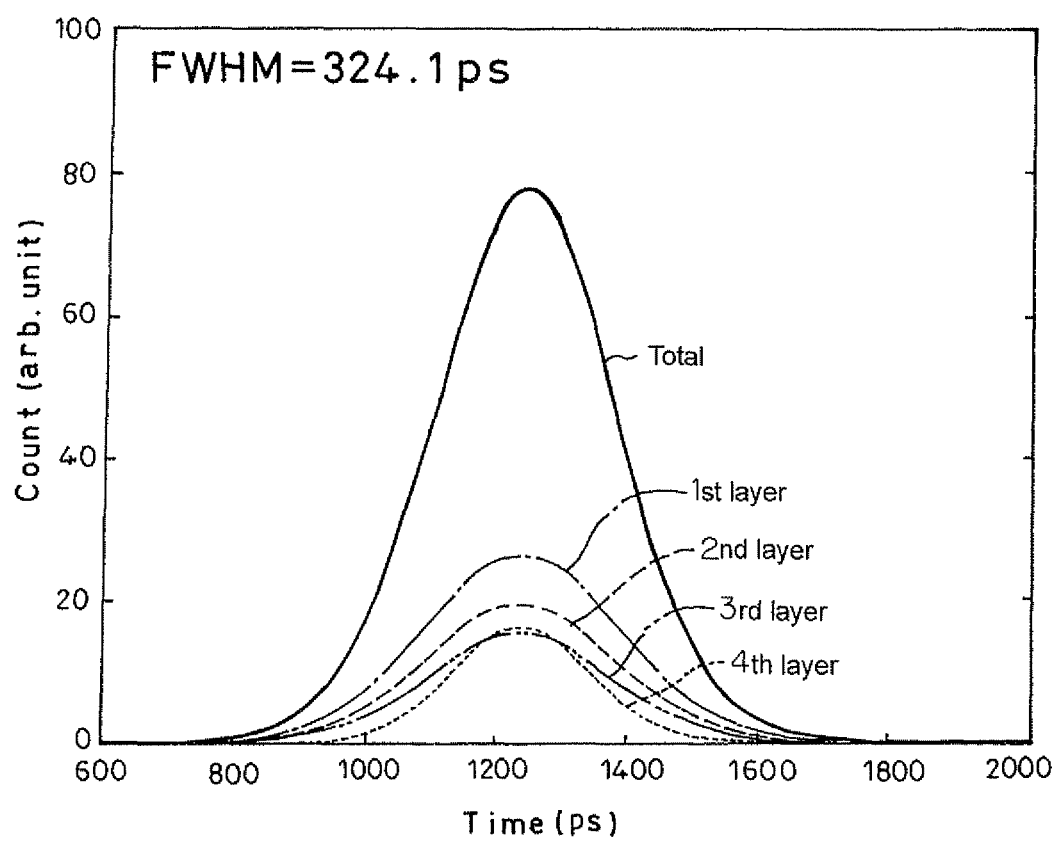
FIG. 6 is a drawing showing responses of individual layers where TOF correction is made in each of these layers and the time resolution of the detector as a whole.
Figure 7:
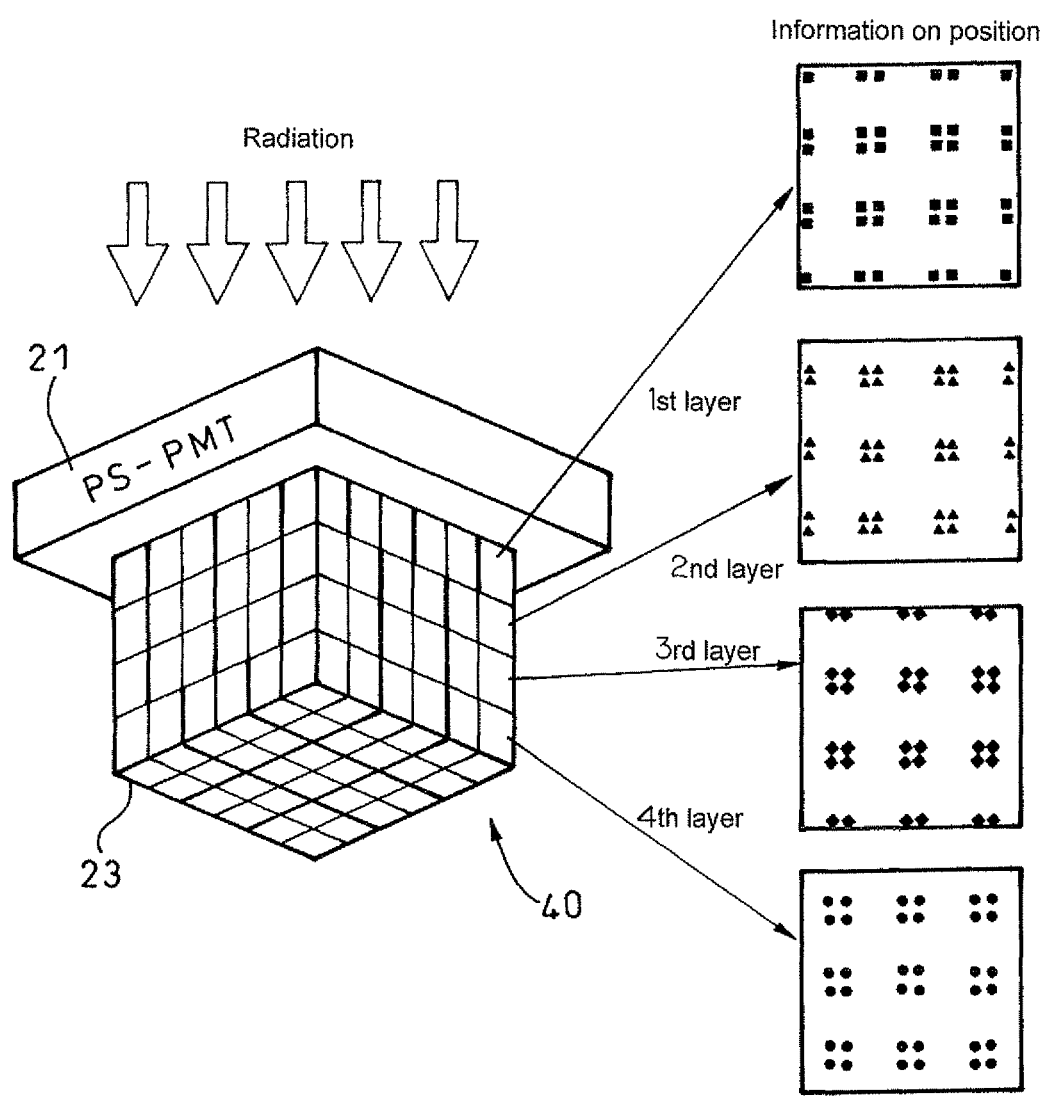
FIG. 7 is a perspective view for explaining the principal of the present invention.
Figure 8:
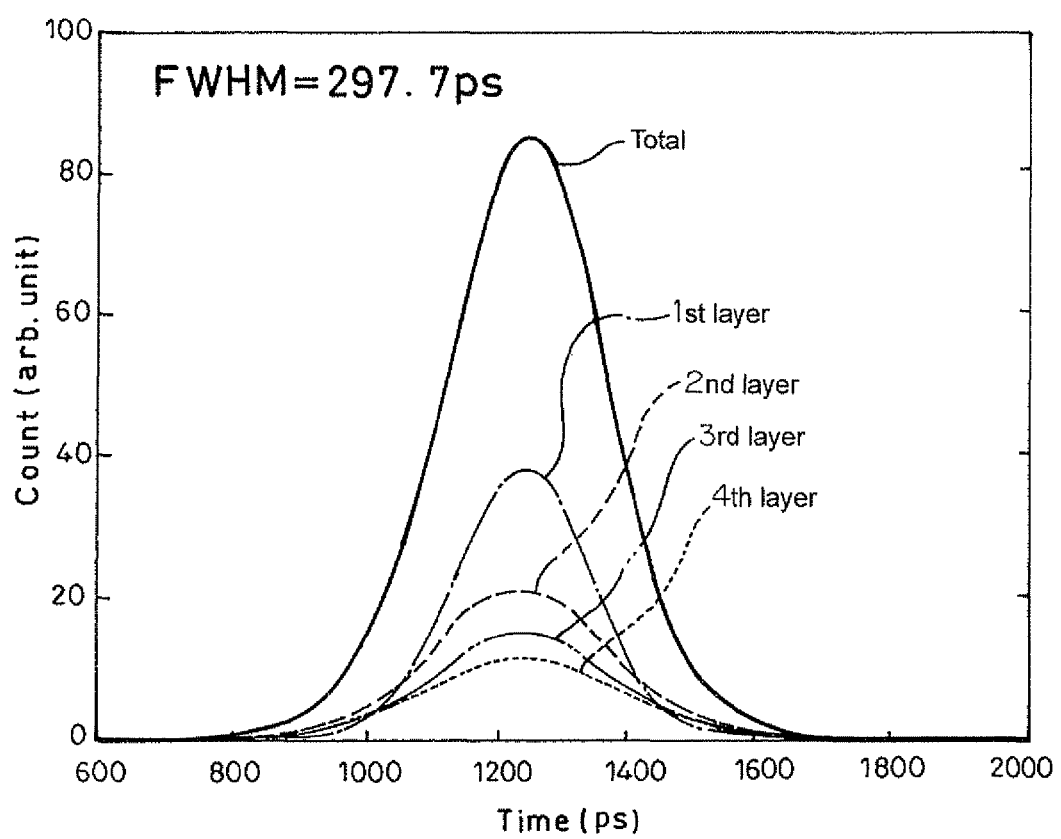
FIG. 8 is a drawing for showing responses of individual layers and the time resolution of the detector as a whole in the example shown in FIG. 7.
Figure 9:
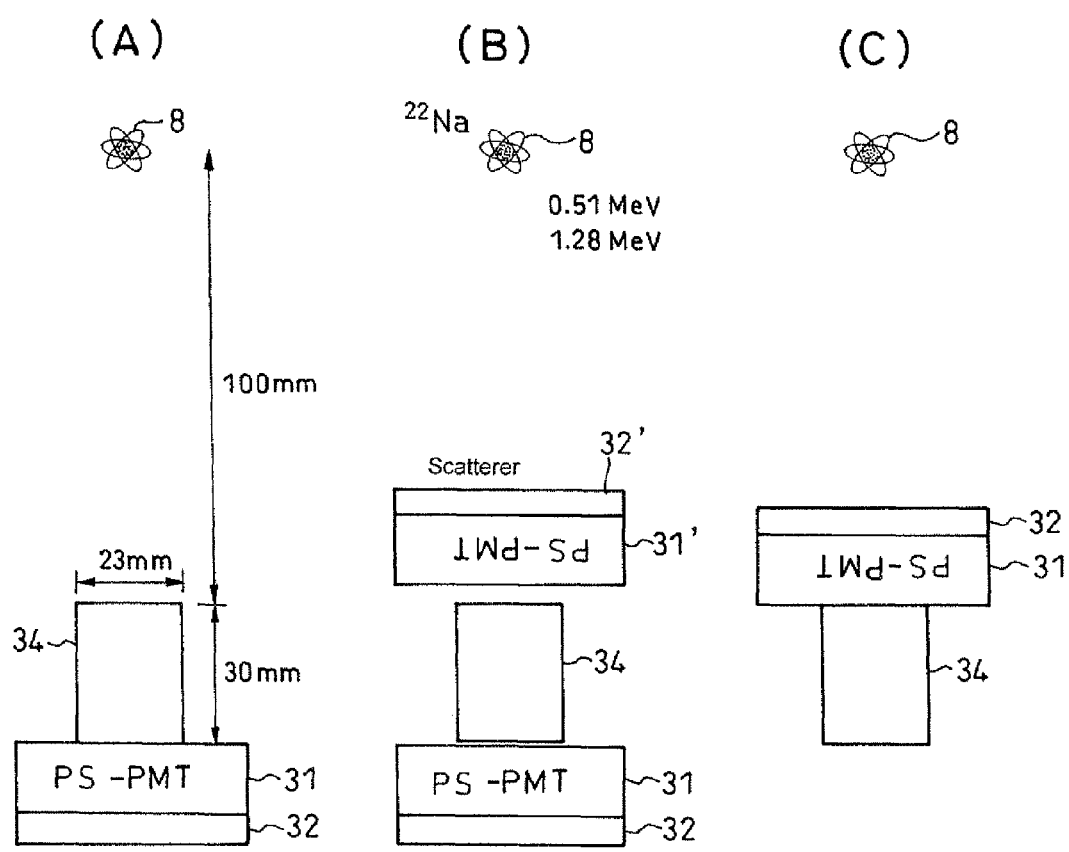
FIG. 9 is a drawing showing arrangements made in an experiment for confirmation.
Figure 10:
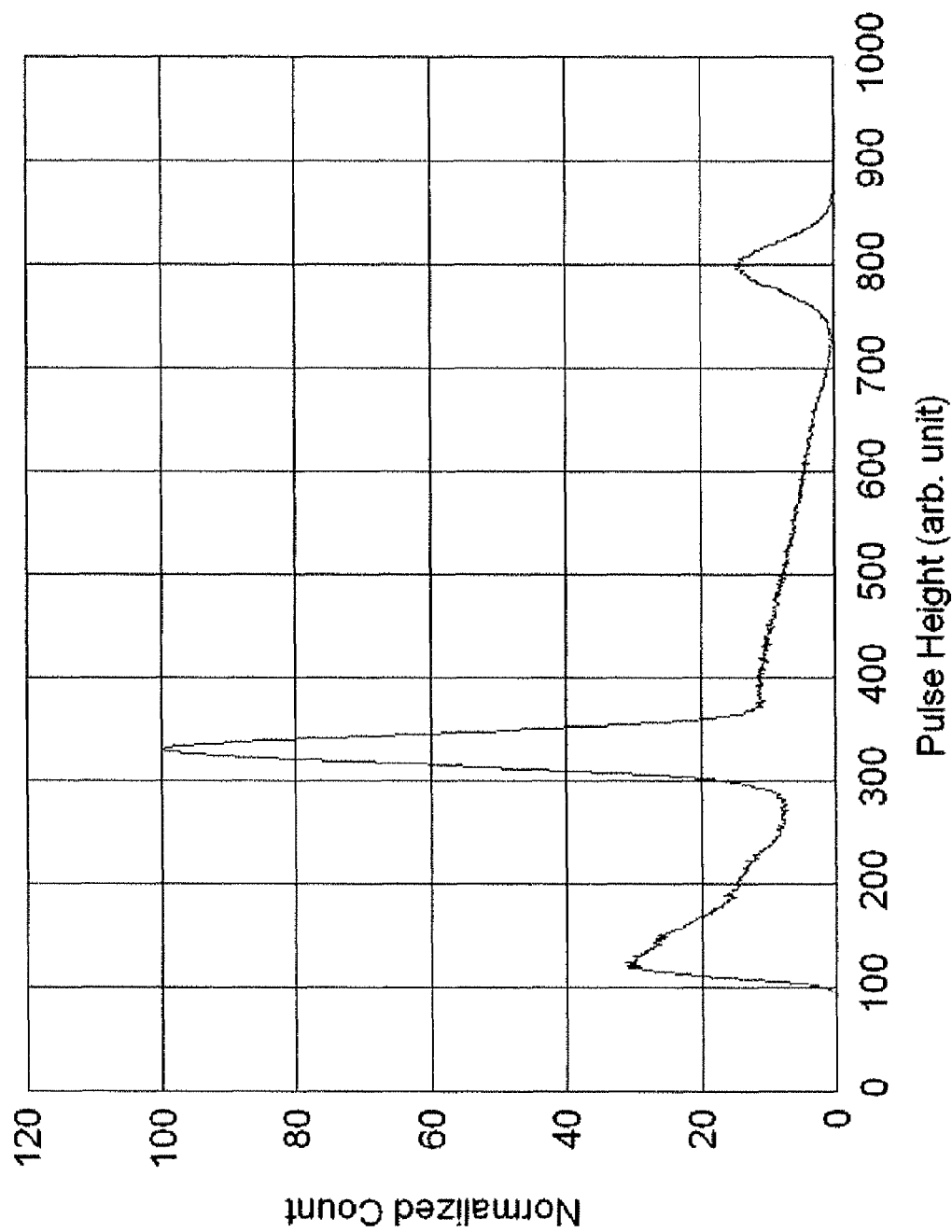
FIG. 10 is a drawing showing a result of the experiment for a conventional arrangement.
Figure 11:
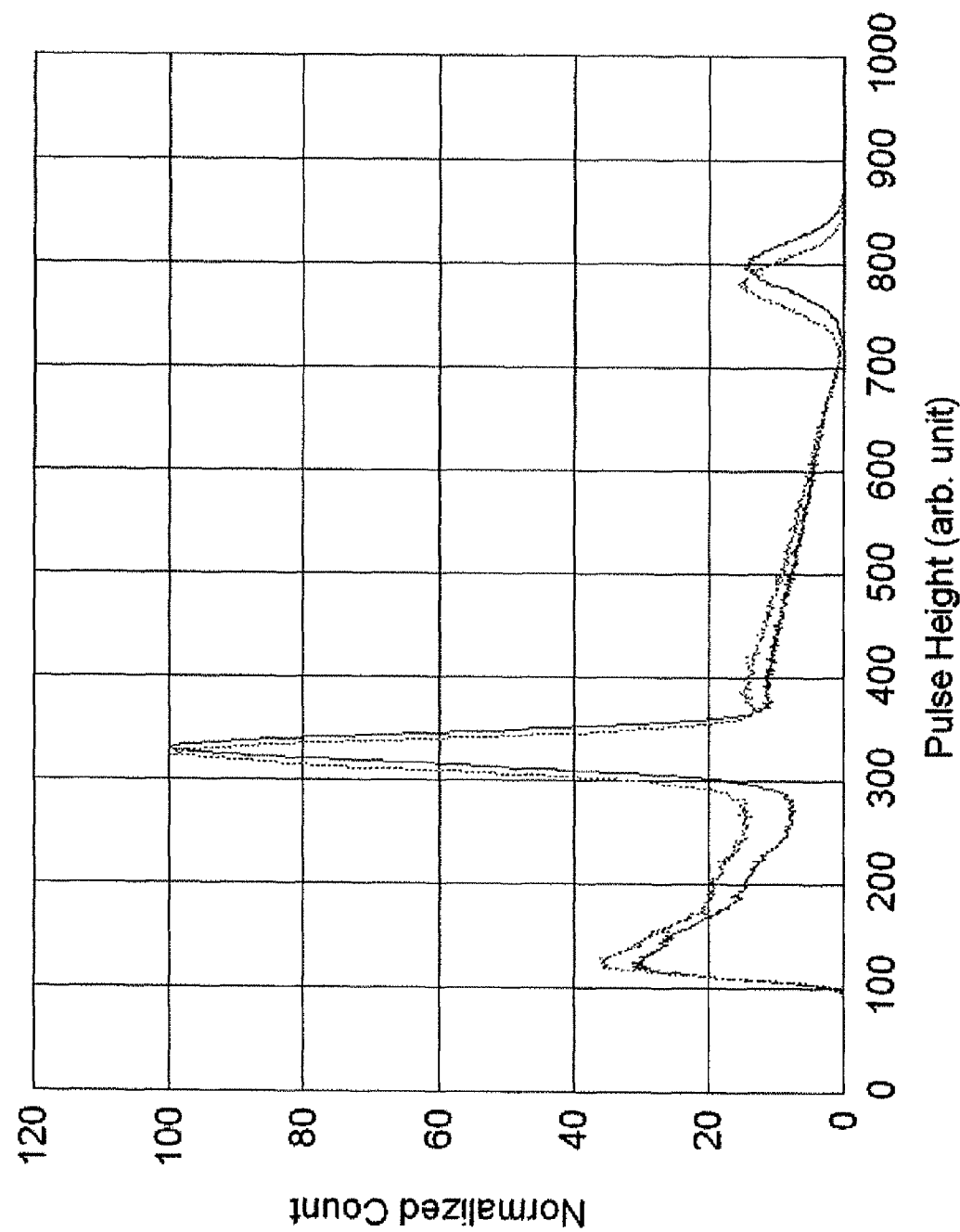
FIG. 11 is a drawing showing a result of the experiment for an arrangement of a comparative example.
Figure 12:
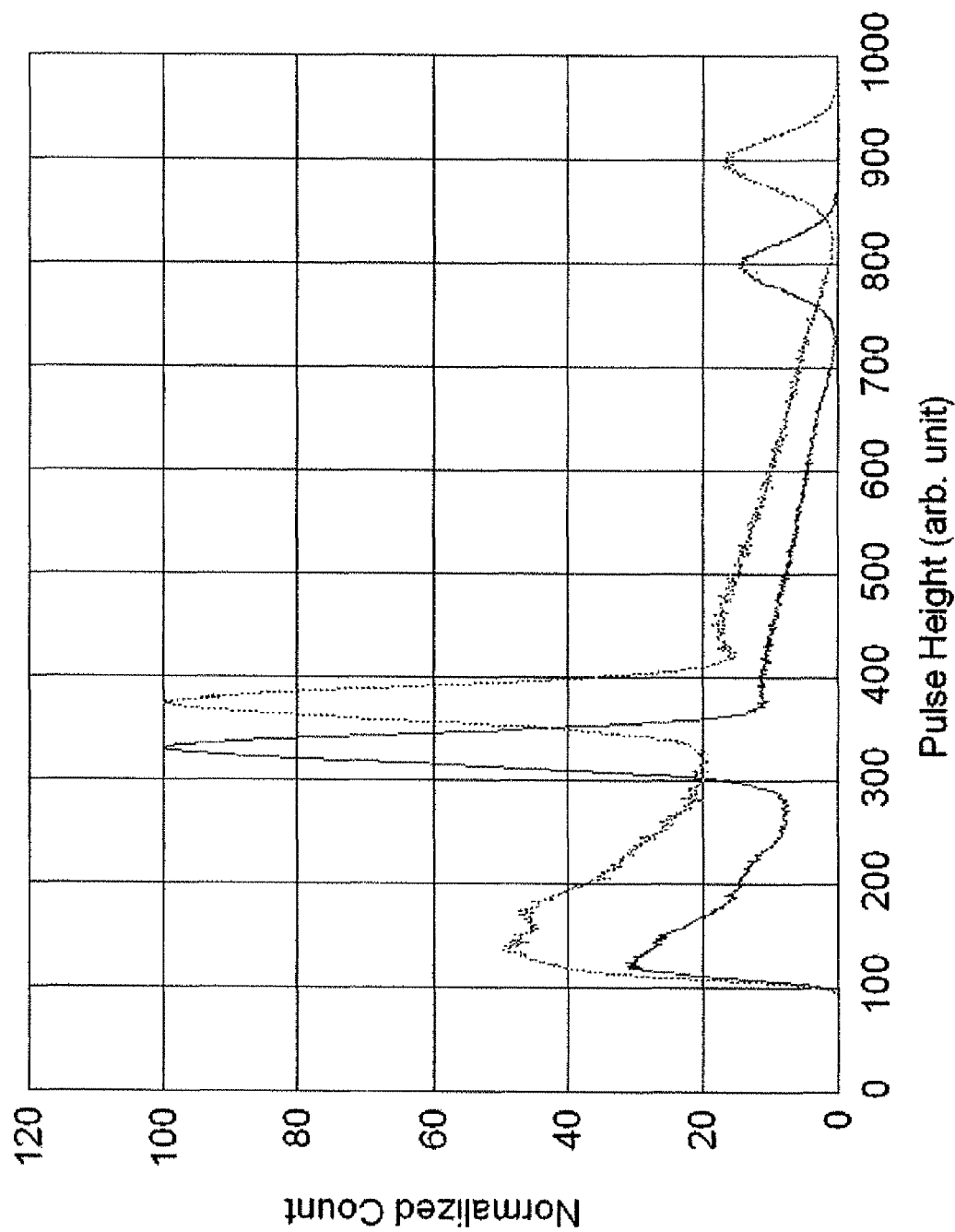
FIG. 12 is a drawing showing a result of the experiment in an arrangement of the present invention.
Figure 13:
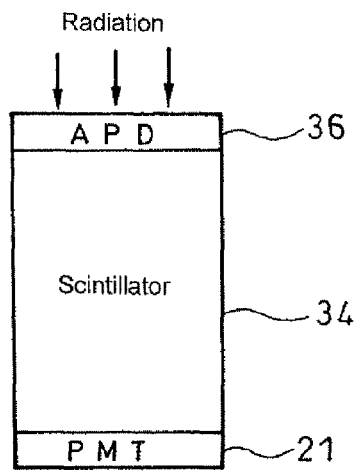
FIG. 13 is a cross sectional view showing a constitution of the other conventional example.

Hereinafter, an explanation will be made in detail for embodiments of the present invention by referring to the drawing.

Figure 14:
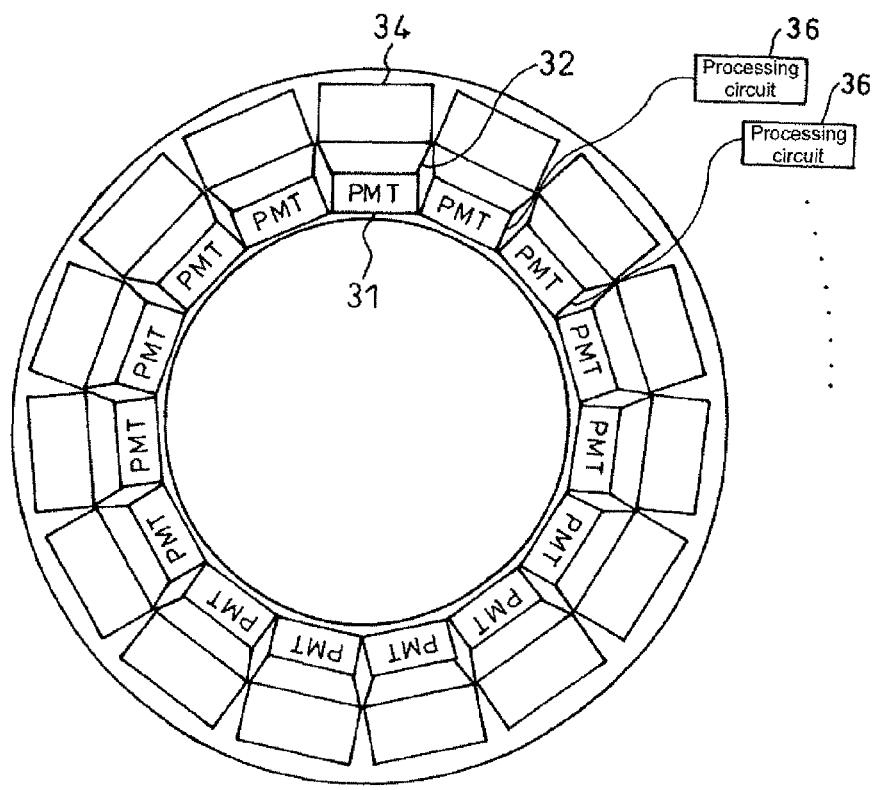
FIG. 14 is a cross sectional view of a PET scanner of Embodiment 1 of the present invention.

As shown in FIG. 14, Embodiment 1 of the present invention is a positron emission tomography scanner in which PMTs 31 are arrayed on the side of a patient, which is a radiation source, scintillators 34 are disposed via light guides 32 outside thereof, and processing circuits 36 at a back stage connected with each of the PMTs 31 are used to identify an incident position, incident time and energy of radiation made incident.

Thereby, it is possible to enhance time resolution and energy resolution.

In the present embodiment, the light guide 32 is installed and a diameter of the light-emitting light path on the side of the PMT 31 is narrowed down with respect to a diameter of the incident light path on the side of the scintillator 34, thus making it possible to arrange the scintillators 34 and the PMTs 31 without any clearance left.

Figure 15:
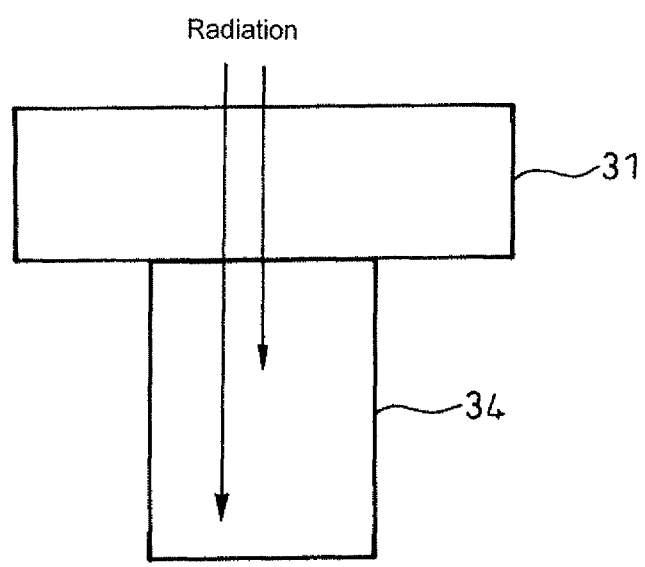
FIG. 15 is a cross sectional view showing a scintillator and a light receiver portion used in Embodiment 2 of the present invention.

In addition, types of the radiation detector are not limited to a DOI detector. As in Embodiment 2 shown in FIG. 15, the scintillators 34 are not stacked in four layers but may be made into a thick one layer, two or three layers, or more than five layers, or the light guide 32 is omitted and the PMT 31 may be directly disposed on the side of a radiation source of the scintillator 34. For example, where the PMT 31 is sufficiently thin or where radiation detectors are not required to be arranged densely, no light guide is needed. Where the light guide is not needed, it is preferably omitted.

Figure 16:
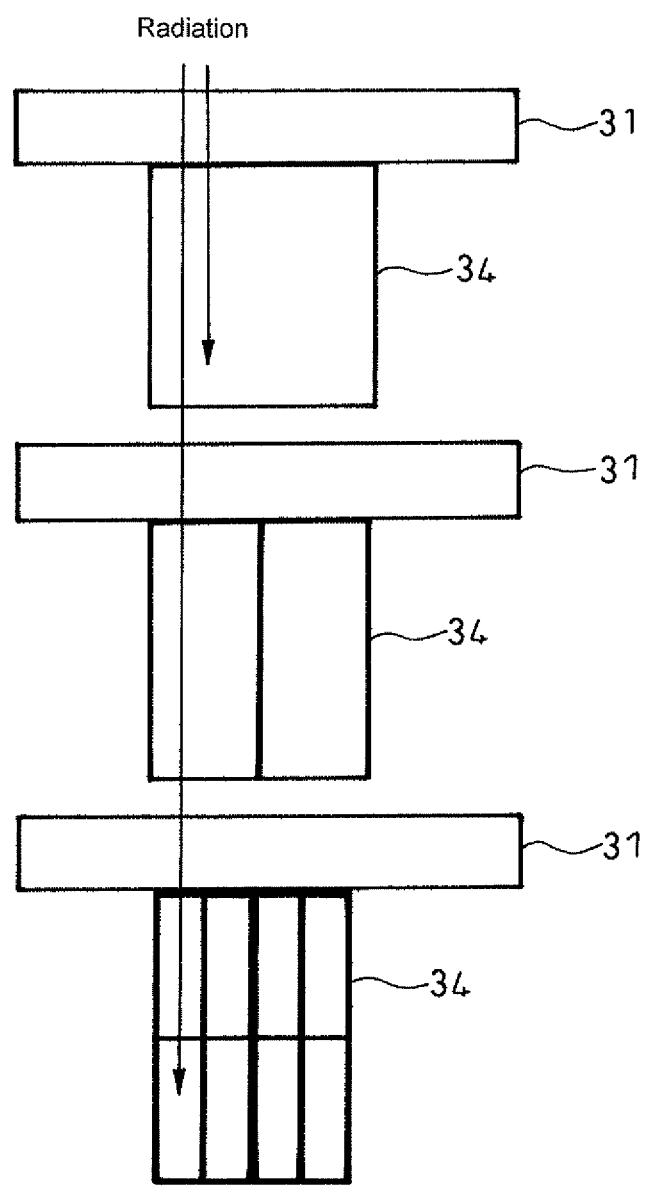
FIG. 16 is a cross sectional view showing a scintillator and a light receiver portion in Embodiment 3 of the present invention.

Further, a combination of the scintillators 34 with the PMTs 31 is not limited to one stage. As in Embodiment 3 shown in FIG. 16, the scintillators 34 are changed in constitution for every stage and can be disposed in a multiple stage. Here, it is acceptable that a relationship between the scintillators 34 and the PMTs 31 is on a one to one basis, on a many to one basis, on a one to many basis and on a many to many basis.

Figure 17:
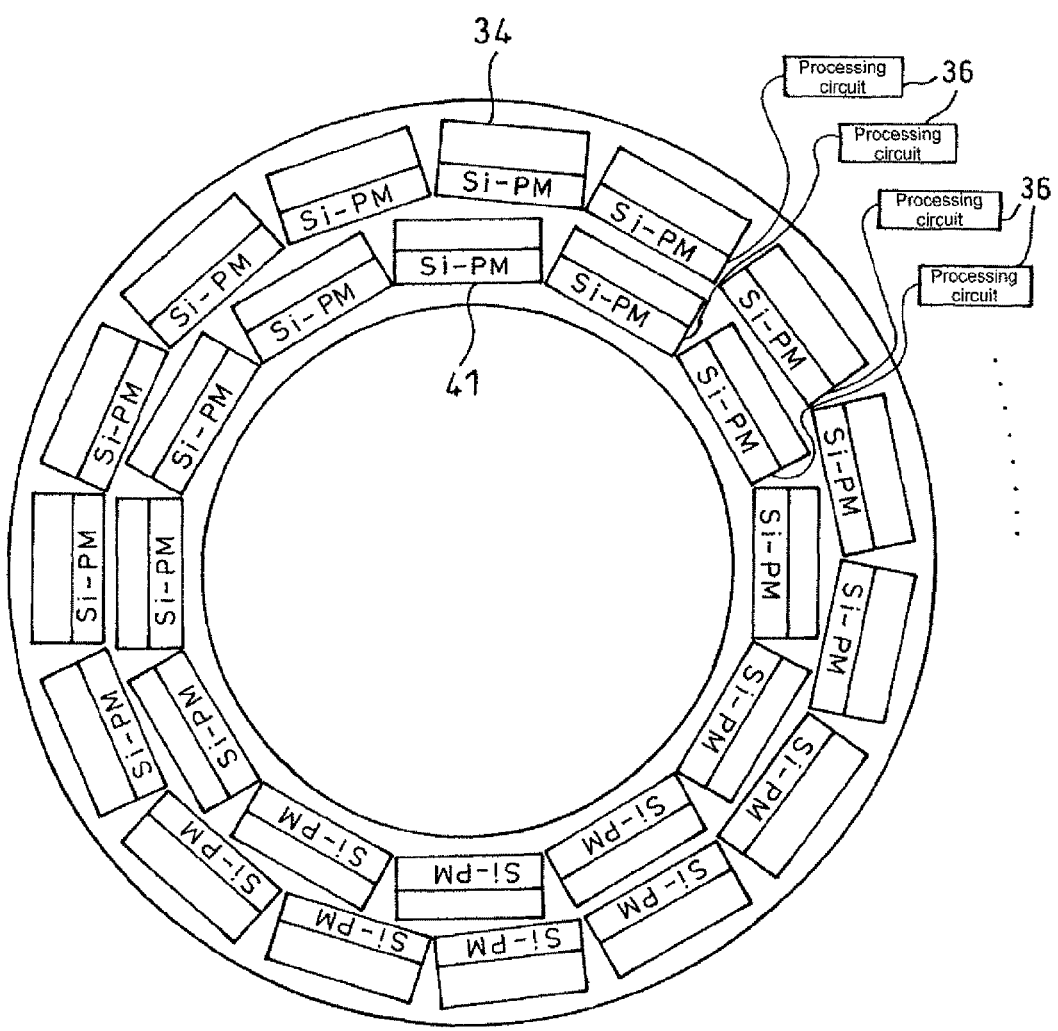
FIG. 17 is a cross sectional view showing a constitution of a PET scanner of Embodiment 4 of the present invention.

Still further, as in Embodiment 4 shown in FIG. 17, as a light receiver, for example, silicon photomultipliers (a Si-PM, that is, an APD working in a Geiger region) 41 can be used and arranged in one layer or two or more layers.

In addition, in the previous embodiments, a PMT and a Si-PM which are thin are used. In general, a light receiver is an element capable of converting a light signal to an electric signal and outputting the signal. Types of the light receiver used in carrying out the present invention are not limited to them but may include other types of elements having similar functions such as a photodiode and an avalanche photodiode.

Further, the scintillator is not necessarily a solid but may be a gas or a liquid. Still further, where the scintillator is a solid, it is not necessarily a single crystal but, for example, may be glass, ceramics or a sintered body. The light-emitting principal of the scintillator may be also Cherenkov radiation.

Further, an object to which the present invention is applied is not limited to a TOF-PET. The object may include an ordinary PET scanner in which, for example, TOF is not utilized. Still further, it may include a SPECT which utilizes relatively high energy (for example, $^{131}$I, 364 keV)

INDUSTRIAL APPLICABILITY

The present invention is applied to a positron emission tomography scanner and others, thus making it possible to identify incident time, an incident position and energy of radiation into a radiation detector at high accuracy.

The invention claimed is:

1. A method for detecting radiation comprising:
    installing a light receiver for detecting incident time adjacent to a side of a radiation source of a scintillator, the scintillator including a Cherenkov radiation emitter; and
    obtaining information on radiation made incident into the scintillator by an output of the light receiver,
    wherein the light receiver receives light and outputs an electrical signal directly, and
    wherein a radiation detector made up of the scintillator and the light receiver is a DOI detector.

2. The method for detecting radiation according to claim 1, wherein the light receiver is installed only on the side of the radiation source of the scintillator.

3. The method for detecting radiation according to claim 1, wherein the light receiver is installed on the side of the radiation source of the scintillator and a detector for obtaining information is installed also on a side part of the scintillator or on an opposite side of the scintillator.

4. The method for detecting radiation according to claim 1, wherein a combination of a plurality of scintillators with a plurality of light receivers are stacked.

5. The method for detecting radiation according to claim 1, wherein a radiation detector to be made a pair is installed so as to be opposite behind the radiation source, thus making it possible to determine coincidence and time of flight.

6. The method for detecting radiation according to claim 1, wherein radiation detectors are arrayed in a ring shape so as to surround the radiation source and a light guide is installed between a scintillator and a light receiver which constitute each of the radiation detectors, thus making it possible to narrow down a diameter of a light-emitting light path with respect to a diameter of an incident light path to the light guide.

7. The radiation detecting device according to claim 1, wherein the light receiver receives only light.

8. A radiation detecting device comprising:
    a light receiver for detecting incident time which is installed adjacent to a side of a radiation source of a scintillator, the scintillator including a Cherenkov radiation emitter; and
    a means for obtaining information on radiation made incident into the scintillator by an output of the light receiver,
    wherein the light receiver receives light and outputs an electrical signal directly, and
    wherein a radiation detector made up of the scintillator and the light receiver is a DOI detector.

9. The radiation detecting device according to claim 8, wherein the light receiver is installed only on the side of the radiation source of the scintillator.

10. The radiation detecting device according to claim 8, wherein the light receiver is installed on the side of the radiation source of the scintillator and a light receiver for obtaining information is installed also on a side part of the scintillator or on an opposite side of the scintillator.

11. The radiation detecting device according to claim 8, wherein a combination of a plurality of scintillators with a plurality of light receivers are stacked.

12. The radiation detecting device according to claim 8, wherein a radiation detector to be made a pair is installed so as to be opposite behind the radiation source, thus making it possible to determine coincidence and time of flight.

13. The radiation detecting device according to claim 8, wherein radiation detectors are arrayed in a ring shape so as to surround the radiation source and a light guide is installed between a scintillator and a light receiver which constitute each of the radiation detectors, thus making it possible to narrow down a diameter of a light-emitting light path with respect to a diameter of an incident light path to the light guide.

14. A positron emission tomography scanner which is provided with the radiation detecting device according to claim 8.

* * * * *